United States Patent [19]
Guskey et al.

[11] Patent Number: 5,840,287
[45] Date of Patent: Nov. 24, 1998

[54] ANTIPERSPIRANT COMPOSITIONS CONTAINING GELLANTS IN THE FORM OF ALKYL AMIDES OF DI- AND TRI-CARBOXYLIC ACIDS

[75] Inventors: Gerald John Guskey, Montgomery; Raymond Joseph Lo; David Frederick Swaile, both of Cincinnati, all of Ohio

[73] Assignee: Procter & Gamble Company, Cincinnati, Ohio

[21] Appl. No.: 771,183

[22] Filed: Dec. 20, 1996

[51] Int. Cl.[6] .............. A61K 7/32; A61K 7/38; A61K 7/34; A61K 7/00
[52] U.S. Cl. .............. 424/65; 424/66; 424/68; 424/400; 424/401; 424/DIG. 5
[58] Field of Search .............. 424/65, 66, 67, 424/68, 400, 401

[56] References Cited

U.S. PATENT DOCUMENTS

| | | | |
|---|---|---|---|
| 2,890,987 | 6/1959 | Hilfer | 167/90 |
| 2,900,306 | 8/1959 | Slater | 167/90 |
| 3,255,082 | 6/1966 | Barton | 167/90 |
| 3,792,068 | 2/1974 | Luedders | 556/27 |
| 3,887,692 | 6/1975 | Gilman | 423/462 |
| 3,903,258 | 9/1975 | Siegal | 424/66 |
| 3,904,741 | 9/1975 | Jones et al. | 423/462 |
| 3,969,087 | 7/1976 | Saito et al. | 44/7 C |
| 3,970,748 | 7/1976 | Mecca | 424/68 |
| 3,979,510 | 9/1976 | Rubino | 424/47 |
| 3,981,896 | 9/1976 | Pauling | 556/10 |
| 4,017,599 | 4/1977 | Rubino | 424/47 |
| 4,049,792 | 9/1977 | Elsnau | 424/66 |
| 4,053,581 | 10/1977 | Pader et al. | 424/68 |
| 4,126,679 | 11/1978 | Davy et al. | 424/66 |
| 4,137,306 | 1/1979 | Rubino | 424/68 |
| 4,147,766 | 4/1979 | Kozischek | 424/14 |
| 4,151,272 | 4/1979 | Geary | 424/68 |
| 4,154,816 | 5/1979 | Roehl et al. | 424/68 |
| 4,202,879 | 5/1980 | Shelton | 424/66 |
| 4,226,889 | 10/1980 | Yuhas | 424/59 |
| 4,371,645 | 2/1983 | Mahaffey, Jr. | 524/108 |
| 4,425,328 | 1/1984 | Nabial | 424/68 |
| 4,429,140 | 1/1984 | Murial et al. | 549/370 |
| 4,518,582 | 5/1985 | Schamper et al. | 424/66 |
| 4,639,369 | 1/1987 | Ciaudelli | 424/59 |
| 4,719,102 | 1/1988 | Randhawa et al. | 424/66 |
| 4,722,835 | 2/1988 | Schamper et al. | 424/66 |
| 4,725,430 | 2/1988 | Schamper et al. | 424/66 |
| 4,725,432 | 2/1988 | May | 424/66 |
| 4,743,444 | 5/1988 | Mccall | 424/66 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,822,603 | 4/1989 | Farris et al. | 424/66 |
| 4,919,934 | 4/1990 | Deckner et al. | 424/402 |
| 4,944,937 | 7/1990 | McCall | 424/65 |
| 4,944,938 | 7/1990 | Potini | 424/66 |
| 4,948,578 | 8/1990 | Burger et al. | 424/68 |
| 4,980,156 | 12/1990 | Raleigh et al. | 424/66 |
| 4,985,238 | 1/1991 | Tanner et al. | 424/66 |
| 4,987,243 | 1/1991 | Kawam et al. | 556/27 |
| 5,019,375 | 5/1991 | Tanner et al. | 424/66 |
| 5,023,354 | 6/1991 | Salome et al. | 549/364 |
| 5,102,656 | 4/1992 | Kasat | 424/66 |
| 5,106,999 | 4/1992 | Gardlik et al. | 549/364 |
| 5,156,834 | 10/1992 | Beckmeyer et al. | 424/47 |
| 5,169,626 | 12/1992 | Tanner et al. | 424/66 |
| 5,200,127 | 4/1993 | Gardlik et al. | 424/66 |
| 5,346,694 | 9/1994 | Juneja | 424/66 |
| 5,384,117 | 1/1995 | Vu et al. | 424/66 |
| 5,429,816 | 7/1995 | Hofrichter et al. | 424/66 |
| 5,449,511 | 9/1995 | Coe | 424/66 |
| 5,455,026 | 10/1995 | Bahr et al. | 424/65 |
| 5,480,637 | 1/1996 | Smith | 424/78.02 |
| 5,486,566 | 1/1996 | Katsoulis | 524/773 |
| 5,492,691 | 2/1996 | Bahr et al. | 404/65 |
| 5,500,209 | 3/1996 | Ross et al. | 424/66 |
| 5,531,986 | 7/1996 | Shevade et al. | 424/68 |
| 5,552,136 | 9/1996 | Motley | 424/68 |

FOREIGN PATENT DOCUMENTS

| | | |
|---|---|---|
| 1266003 | 4/1986 | Canada . |
| 2054478 | 5/1992 | Canada . |
| 0 295 070 | 12/1988 | European Pat. Off. . |
| 0 295 071 | 12/1988 | European Pat. Off. . |
| 0 396 137 | 11/1990 | European Pat. Off. . |
| 0 448 278 | 9/1991 | European Pat. Off. . |
| 530866 A1 | 3/1993 | European Pat. Off. . |
| 0 616 842 A1 | 9/1994 | European Pat. Off. . |
| 0 682 940 A1 | 11/1995 | European Pat. Off. . |
| 61 206 450 | 9/1986 | Japan . |
| 62-265393 | 11/1987 | Japan . |
| 10-20286 | 1/1989 | Japan . |
| 64-62377 | 3/1989 | Japan . |
| 1-207223 | 8/1989 | Japan . |
| 2-180805 | 7/1990 | Japan . |
| 2-264707 | 10/1990 | Japan . |
| 3-170415 | 7/1991 | Japan . |
| A 42 08 202 | 7/1992 | Japan . |
| 1485694 | 9/1977 | United Kingdom . |
| 2253347 | 9/1992 | United Kingdom . |
| 2299024 | 9/1996 | United Kingdom . |
| WO 96/26709 | 9/1996 | WIPO . |

OTHER PUBLICATIONS

M. F. Bobin, C. Suzza and M–C. Martini, "Using Fluorinated Compounds in Topical Preparations", 111 *Cosmetics and Toiletries* 47–63, Oct., 1996.

Taro Tachibana and Hideko Kambara, "Studies of Helical Aggregates of Molecules. I. Enantiomorphism in the Helical Aggregates of Optically Active 12–Hydroxystearic Acid and Its Lithium Salt", *Bulletin of the Chemical Society of Japan*, vol. 42, 3422–3424 (1969).

(List continued on next page.)

*Primary Examiner*—Shelly A. Dodson
*Attorney, Agent, or Firm*—William J. Winter; Tara M. Rosnell; David L. Suter

[57] ABSTRACT

The present invention relates to antiperspirant compositions in the form of gels and gel-solids. In particular, the present invention relates to select compositions in the form of gels that provide improved residue characteristics and efficacy performance.

17 Claims, No Drawings

OTHER PUBLICATIONS

Taro Tachibana Shyoko Kitazawa and Hideko Takeno, "Studies of Helical Aggregates of Moleculers. II, The Sense of Twist in the Fibrous Aggregates from the Alkali Metal Soaps of Optically Active 12–Hydroxystearic Acid", *Bulletin of the Chemical Society of Japan*, vol. 43 2418–2421 (1970).

"Electron Microscopes and Thermal Studies of Optically Active 12–Hydroxystearic Acids in Soap Formation", *Journal of Colloid and Interface Science*, vol. 51, No. 2, May 1975.

"Morphology of Collapsed Monolayers of Optically Active and Racemic 12–Hydroxystearic Acids", *Journal of Colloid and Interface Science*, vol. 61, No. 2, Sep. 1977.

C. D. Vaughn, "Solubility Effects in Product, Package, Penetration and Preservation" 103 *Cosmetics and Toiletries* 47–69, Oct., 1988.

Plechner, *Antiperspirants and Deodorants,* 2 Cosmetics, Science and Technology, Balsam and Sagarin, 374–400, 1972.

Homma, Masao, Oil Gelating Agent Utilizing Amino Acids, (Modern Chemistry), 54–59, Aug., 1987 (Translation).

C. D. Vaughn, "Using Solubility Parameters in Cosmetics Formulation", *J. Soc. Cosmetic Chemists* 319–333 Sep./Oct., 1985.

Tsau, Heller and Pratap, "Thermoreversible Organogels of 12–Hydroxystearic Acid", *Polymer Preprints* 1994 35, 737–738.

Balsam and Sagarin, Cosmetics, Science, and Technology, vol. 1, 27–104, 1972.

Geria, "Formulation of Stick Antiperspirants and Deodorants", *Cosmetics and Toiletries*, 99:55–60 (1984).

Gels and Sticks Formulary, 99 *Cosmetics and Toiletries* 82–87, 1984.

Todd et al., "Volatile Silicone Fluids for Cosmetics", *Cosmetics and Toiletries*, 91:29–32 (1976).

Chemical Abstracts, vol. 85, No. 2, Jul. 12, 1976 No. 85:10310.

Taro Tachibana, Tomoko Mori and Kayako Hori, "New type of twisted mesophase in jellies and solid films of chiral 12–hydroxyoctadecanoic acid", *Nature*, vol. 278, Apr. 1979.

Tachibana, Mori and Hori, "Chiral Mesophases of 12–Hydroxyoctadecanoic Acid in Jelly and in the Solid State. II. A new Type of Mesomorphic Solid State", *Bulletin of the Chemical Society of Japan*, vol. 54, 73–80 (1981).

Ito, Yudasaka and Fujtyama, "Light Scattering Study of the 12–Hydroxyoctadecanoic Acid and Benzane Mixture in the Gel State", *Bulletin of the Chemical Society of Japan*, vol. 54, 1939–1942 (1981).

Tamura, Suetake, Ohkubo and Ohbu, "Effect of Alkali Metal Ions on Gel Formation in the 12–Hydroxystearic Acid/ Soybean Oil System", JAOCS, vol. 71, No. 8 (Aug. 1994).

Cebula and Smith, "Differential Scanning Calorimetry of Confectionery Fats. Pure triglycerides: Effects of Cooling and Heating Rate Variation", JAOCS, vol. 68 No. 8 (Aug. 1991).

Taro Tachibana, Tomoko Mori, and Kayako Hori, "Chiral Mesophases of 12–Hydroxyoctadecanoic Acid in Jelly and in the Solid State. I. A New Type of Lyotropic Mesophase in Jelly with Organic Solvents", *Bulletin of the Chemical Society of Japan*, vol. 53, No. 6, 1714–1719 (1980).

ANTIPERSPIRANT COMPOSITIONS CONTAINING GELLANTS IN THE FORM OF ALKYL AMIDES OF DI- AND TRI-CARBOXYLIC ACIDS

TECHNICAL FIELD

The present invention relates to antiperspirant compositions in the form of gels or gel-solids. In particular, the present invention relates to select compositions in the form of gels or gel-solids that provide improved residue characteristics and efficacy performance.

BACKGROUND OF THE INVENTION

Personal hygienic habits typically include routine bodily washings followed by the application of odor retarding and/or moisturizing skin actives. Cosmetic compositions used to deliver such actives generally take the form of hard gel sticks or soft gels. Incorporating cosmetic ingredients into soft gel or gel stick carriers tends to enhance the overall perceived "elegance" of such compositions.

Currently, gel stick carriers dominate the U.S. antiperspirant market, constituting more than 50% of total antiperspirant sales, and is popular to varying degrees globally. Cosmetically acceptable sticks typically contain a solvent vehicle such as cyclomethicone together with a waxy substance such as stearyl alcohol, alone or in combination with castor wax, to gel or thicken the suspension sufficiently to create a suitable stick.

The stick form is distinguished from gels or pastes in that the stick can maintain its shape for extended time periods outside the package (although some shrinkage occurs due to solvent evaporation). Alternatively, one can adjust the amount of stearyl alcohol and castor wax or include silicas or other inorganic gelling agents to produce a viscous gel or paste in place of the stick. These gels or pastes can be suitably packaged in containers which have the appearance of a stick, but which dispense through apertures on the top surface of the package. These products are typically called soft sticks or "smooth-ons". A more detailed description of soft gels is found in U.S. Pat. No. 5,102,656 to Kasat, U.S. Pat. No. 5,069,897 to Orr, and U.S. Pat. No. 4,937,069 to Shin, each of which are herein incorporated by reference in their entirety.

An important disadvantage of hard stick carriers relates to a visible residue left on the skin during or after application. This visible residue tends to stain fabrics and is, therefore, considered undesirable by consumers. Furthermore, in formulating gel stick carriers, the active ingredients are typically suspended in a vehicle such as cyclomethicone. Such suspensions generally result in syneresis and/or weeping problems which adversely affect formula stability and aesthetic properties; this is particularly true when shipping in warm climates and/or high altitudes.

Attempting to address these concerns, researchers have suggested varying the type of gelling agent used. One proposal involved the use of dibenzylidene alditols. One problem with Dibenzylidene alditols, however, relates to the inherent instability of such compounds in acidic environments. Moreover, antiperspirant sticks which combined such gelling agents with solubilized antiperspirant actives resulted in antiperspirant sticks having a tacky skin feel and poor efficacy.

Another attempt involved the use of n-acyl amino acid gelling agents. Information regarding the use of these gelling agents is found in: U.S. Pat. No. 3,969,087 issued on Jul. 13, 1976 to Saito et al.; Japanese Patent Application 1-207223, published Aug. 21, 1989; Japanese Patent Application 1-207223 which published Aug. 21, 1989; and Japanese Patent Application 2-180805 which published Jul. 13, 1988.

While the prior art discloses a variety of gelling agents useful in formulating soft gel or gel stick compositions, there is still a need for additional formulations which reduce the visible residue associated with such compositions. The present inventors have found that soft gel or gel-solid stick compositions that incorporate gelling agents which provide crystal structures resembling that of "tuning fork", such as alkyl amides of di- and tri-basic carboxylic acids or anhydrides, provide such reduced visible residue compositions.

Accordingly, it is an object of the present invention to provide improved antiperspirant compositions.

It is also an object of the present invention to provide improved antiperspirant compositions in the form of a gel or gel-solid stick.

It is another object of the present invention to provide improved gel-solid stick or gel antiperspirant compositions further comprising an antiperspirant active.

It is a further object of the present invention to provide improved gel-solid stick or gel antiperspirant compositions for reducing body malodor, containing an antiperspirant active and gelling agent, having good structural integrity with reduced visible residue.

A still even further object of the present invention to provide methods for delivering antiperspirant actives.

These and other objects will become readily apparent from the disclosure which follows.

SUMMARY OF THE INVENTION

An antiperspirant gel composition comprising:

A.) an antiperspirant active;

B.) a gellant of the formula:

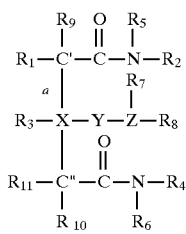

a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl;

g) X is nil, nitrogen, aryl or 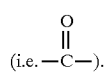 where n is an integer from 1 to 6;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl; and j) "a" is a double or single bond provided:
(i) when X is nil, Y, Z, $R_3$, $R_7$ and $R_8$ are nil, C' is bonded directly to C" and $R_1$ is not a hydrogen;
(ii) when X and Z are not nil and Y is nil, X is directly bonded to Z;
(iii) when Z is nil, a hydrogen or a hydroxy, $R_7$ and $R_8$ are nil; and
(iv) when "a" is a double bond, $R_3$ and $R_9$ are nil; and C.) an anhydrous liquid carrier.

By "acyl" or "carbonyl" as used herein means a radical formed by removal of the hydroxy and alkyl portions of a carboxylic acid $$\text{(i.e. } -\overset{\text{O}}{\underset{\|}{\text{C}}}- \text{).}$$

By "alkyl" as used herein, means an unsubstituted or substituted saturated hydrocarbon chain radical having from 1 to 22 carbon atoms, preferably from 1 to 8 carbon atoms. Preferred alkyl groups include, but are not limited to, methyl, ethyl, propyl, isopropyl, butyl, hexyl and octyl.

By "alkenyl" as used herein, means an unsubstituted or substituted hydrocarbon chain radical having from 2 to 22 carbon atoms, preferably from 2 to 8 carbon atoms, and having at least one olefinic double bond.

By "aryl" as used herein, means an aromatic carbocyclic ring radical. Preferred aryl groups include, but are not limited to, phenyl, tolyl, xylyl, cumenyl and naphthyl.

By "alkoxy" as used herein, means an oxygen radical having a hydrocarbon chain substituent, where the hydrocarbon chain is an alkyl or alkenyl (i.e., —O—alkyl or —O—alkenyl). Preferred alkoxy groups include, but are not limited to, methoxy, ethoxy, propoxy and allyloxy.

By "siloxane" as used herein, means a linear compound consisting of silicon atoms single-bonded to oxygen and so arranged that each silicon atom is linked with two or four oxygen atoms (i.e., —Si(O)$_2$RR' where R and R', independently, are, but not limited to, alkyls, alkyl esters or alkyl ethers).

By "cyclic chain" as used herein,. means an unsubstituted or substituted, saturated, unsaturated or aromatic, hydrocarbon chain ring radical. The cyclic chains are monocyclic or are fused, bridged or spiro polycyclic ring systems.

As defined above and as used herein, substituent groups may themselves be substituted. Such substitution may be with one or more substituents. Such substituents include (for example) those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyacyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

DETAILED DESCRIPTION OF THE INVENTION

The antiperspirant gel or gel-solid stick compositions of the present invention are anhydrous systems which are dispersions of antiperspirant active held or contained within gel matrix.

The term "anhydrous" as used herein means that the antiperspirant gel or gel-solid stick composition of the present invention, and the essential or optional components thereof other than the antiperspirant active, are substantially free of added or free water. From a formulation standpoint, this means that the antiperspirant gel or gel-solid stick compositions of the present invention preferably contain less than about 5%, preferably less than about 3%, more preferably less than about 1%, most preferably zero percent, by weight of free or added water, other than the water of hydration typically associated with the antiperspirant active prior to formulation.

The term "ambient conditions" as used herein refers to surrounding conditions under about one atmosphere of pressure, at about 50% relative humidity, and at about 25° C., unless otherwise specified.

The antiperspirant gel or gel-solid stick compositions of the present invention can comprise, consist of, or consist essentially of the essential elements and limitations of the invention described herein, as well as any of the additional or optional ingredients, components, or limitations described herein.

As percentages, parts and ratios are by weight of the total composition, unless otherwise specified. All such weights as they pertain to listed ingredients are based on the specific ingredient level and, therefore, do not include solvents, carriers, by-products, filler or other minor ingredients that The essential as well as optional components of the compositions of the present invention are described in the following paragraphs.

ESSENTIAL COMPONENTS

Antiperspirant Active

The antiperspirant gel or gel-solid stick compositions of the present invention comprise antiperspirant actives suitable for application to human skin. The concentration of the actives in the composition should be sufficient to provide the desired perspiration wetness and odor control from the antiperspirant gel formulation selected.

The antiperspirant gel or gel-solid stick compositions of the present invention preferably comprise the antiperspirant active at concentrations of from about 0.5% to about 60%, more preferably from about 5% to about 35%, by weight of the composition. These weight percentages are calculated on an anhydrous metal salt basis exclusive of water and any complexing agents such as glycine, glycine salts, or other complexing agents.

The antiperspirant active as formulated in the composition is preferably in the form of dispersed solid particles which are substantially unsolubilized in the anhydrous or substantially anydrous systems described herein. The particulate antiperspirant actives preferably have an average particle size or diameter of less than about 100 μm, more preferably from about 15 μm to about 100 μm, even more preferably from about 20 μm to about 100 μm. Also preferred are dispersed solid particles having an average particle size or diameter of less than about 2 μm, even more preferably from less than about 0.4 μm. It has been found that antiperspirant active particles within the preferred particle size ranges provide lower visible residue performance from the gel compositions herein than other less preferred particle size ranges.

The antiperspirant active for use in the antiperspirant gel or gel-solid stick compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum hydroxyhalides, aluminum chlorohydrate, zirconyl oxyhalides, zirconyl hydroxyhalides, and mixtures thereof.

Preferred aluminum salts for use in the antiperspirant gel or gel-solid stick compositions include those which conform to the formula:

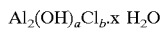
$$Al_2(OH)_aCl_b \cdot x\ H_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant gel or gel-solid stick compositions include those which conform to the formula:

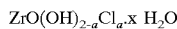
$$ZrO(OH)_{2-a}Cl_a \cdot x\ H_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. 4,120,948, Shelton, issued Oct. 17, 1978, all of which are incorporated herein by reference.

The antiperspirant gel or gel-solid stick compositions of the present invention can also be formulated to comprise other dispersed solids or other materials in addition to or in place of the antiperspirant active. Such other dispersed solids or other materials include any material known or otherwise suitable for topical application to human skin. The anhydrous gel compositions can, therefore, also be formulated as a cosmetic gel which contains no antiperspirant active material, particulate or otherwise.

Gellant

Another essential ingredient of the present invention are gelling agents in the form of alkyl amides of a di- and/or tri-basic carboxylic acids or anhydrides. Alkyl amides suitable for use in the present invention generally have the formula:

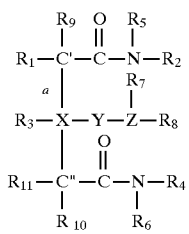

wherein a backbone is formed from the linkage of C', C" and X and wherein a) $R_1$ is nil, hydroxy, hydrogen, aryl, siloxane or saturated or unsaturated, substituted or unsubstituted, straight, branched or cyclic chain $C_1-C_{22}$ alkyl, $C_1-C_{22}$ alkenyl, $C_1-C_{22}$ alkoxy, $C_1-C_{22}$ alkyl esters, $C_1-C_{22}$ alkyl ethers, or $C_1-C_{22}$ alkyl substituted aryl, preferably $C_4-C_{18}$ alkyl, $C_4-C_{18}$ alkenyl, $C_4-C_{18}$ alkoxy, $C_4-C_{18}$ alkyl esters, $C_4-C_{18}$ alkyl ethers, or $C_4-C_{18}$ alkyl substituted aryl, more preferably $C_{12}-C_{18}$ alkyl, $C_{12}-C_{18}$ alkenyl, $C_{12}-C_{18}$ alkoxy, $C_{12}-C_{18}$ alkyl esters, $C_{12}-C_{18}$ alkyl ethers, or $C_{12}-C_{18}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1-C_{22}$ alkyl, $C_1-C_{22}$ alkenyl, $C_1-C_{22}$ alkoxy, $C_1-C_{22}$ alkyl esters, $C_1-C_{22}$ alkyl ethers, or $C_1-C_{22}$ alkyl substituted aryl, preferably $C_4-C_{10}$ alkyl, $C_4-C_{10}$ alkenyl, $C_4-C_{10}$ alkoxy, $C_4-C_{10}$ alkyl esters, $C_4-C_{10}$ alkyl ethers, or $C_4-C_{10}$ alkyl substituted aryl, more preferably $C_4-C_8$ alkyl, $C_4-C_8$ alkenyl, $C_4-C_8$ alkoxy, $C_4-C_8$ alkyl esters, $C_4-C_8$ alkyl ethers, or $C_4-C_8$ alkyl substituted aryl;

c) $R_3$ is nil, hydroxy, hydrogen, saturated or unsaturated, substituted or unsubstituted, straight, branched or cyclic chain $C_1-C_4$ alkyl, $C_1-C_4$ alkenyl, $C_1-C_4$ alkoxy, $C_1-C_4$ alkyl esters or $C_1-C_4$ alkyl ethers, preferably a $C_1-C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1-C_{22}$ alkyl, $C_1-C_{22}$ alkenyl, $C_1-C_{22}$ alkoxy, $C_1-C_{22}$ alkyl esters, $C_1-C_{22}$ alkyl ethers, or $C_1-C_{22}$ alkyl substituted aryl, preferably $C_4-C_{10}$ alkyl, $C_4-C_{10}$ alkenyl, $C_4-C_{10}$ alkoxy, $C_4-C_{10}$ alkyl esters, $C_4-C_{10}$ alkyl ethers, or $C_4-C_{10}$ alkyl substituted aryl, more preferably $C_4-C_8$ alkyl, $C_4-C_8$ alkenyl, $C_4-C_8$ alkoxy, $C_4-C_8$ alkyl esters, $C_4-C_8$ alkyl ethers, or $C_4-C_8$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1-C_6$ alkyl, $C_1-C_6$ alkenyl, $C_1-C_6$ alkoxy, $C_1-C_6$ alkyl esters, $C_1-C_6$ alkyl ethers, or $C_1-C_6$ alkyl substituted aryl, preferably $C_1-C_4$ alkyl, $C_1-C_4$ alkenyl, $C_1-C_4$ alkoxy, $C_1-C_4$ alkyl esters, $C_1-C_4$ alkyl ethers, $C_1-C_4$ alkyl substituted aryl or hydrogen, more preferably a hydrogen;

g) X is nil, nitrogen, aryl or $-(CH_2)_{\overline{n}}-$ where n is an integer from 1 to 6, preferably $-(CH_2)_{\overline{n}}-$ where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1-C_{22}$ alkyl, $C_1-C_{22}$ alkenyl, $C_1-C_{22}$ alkoxy, $C_1-C_{22}$ alkyl esters, $C_1-C_{22}$ alkyl ethers, or $C_1-C_{22}$ alkyl substituted aryl, preferably $C_4-C_{10}$ alkyl, $C_4-C_{10}$ alkenyl, $C_4-C_{10}$ alkoxy, $C_4-C_{10}$ alkyl esters, $C_4-C_{10}$ alkyl ethers, or $C_4-C_{10}$ alkyl substituted aryl, more preferably $C_4-C_8$ alkyl, $C_4-C_8$ alkenyl, $C_4-C_8$ alkoxy, $C_4-C_8$ alkyl esters, $C_4-C_8$ alkyl ethers, or $C_4-C_8$ alkyl substituted aryl; and j) "a" is a double or single bond provided:
   (i) when X is nil, Y, Z, $R_3$, $R_7$ and $R_8$ are nil, C' is bonded directly to C" and $R_1$ is not a hydrogen;
   (ii) when X and Z are not nil and Y is nil, X is directly bonded to Z;
   (iii) when Z is nil, a hydrogen or a hydroxy, $R_7$ and $R_8$ are nil; and
   (iv) when "a" is a double bond, $R_3$ and $R_9$ are nil.

Alkyl amides of di- and tri-basic carboxylic acids or anhydrides suitable for use in the present invention include alkyl amides of citric acid, tricarballylic acid, aconitic acid, nitrilotriacetic acid, succinic acid and itaconic acid such as 1,2,3-propane tributylamide, 2-hydroxy-1,2,3-propane tributylamide, 1-propene-1,2,3-trioctylamide, N,N',N"-tri (acetodecylamide)amine, 2-dodecyl-N,N'-dihexylsuccinamide, and 2 dodecyl-N,N'-dibutylsuccinamide. Preferred for use in the present invention are alkyl amides of di-carboxylic acids such as di-amides of alkyl succinic acids, alkenyl succinic acids, alkyl succinic anhydrides and alkenyl succinic anhydrides, more preferably 2-dodecyl-N,N'-dibutylsuccinamide.

The alkyl amide gelling agents, preferably, have opposing and substantially parallel terminal chains extending outward from the gelling agent backbone. Without being limited by theory, it is believed that this spacial arrangement, or "tuning fork" structural configuration, facilitates the formation of networks essential to the formulation of gel or gel-solid stick compositions. By the phrase "tuning fork configuration", as used herein means any configuration resembling an article or implement having a handle portion which extends longitudinally at one end to form two prongs. It is also preferred that the terminal chains be linked to the gelling agent backbone by means of acyl-amide linkages wherein the acyl portion of the acyl-amide linkage is directly attached to the gelling agent backbone.

The alkyl amides of the present invention are synthesized using either of the following one or two step reaction procedures.

The one step procedure involves direct amidation of the di- or tri-basic organic acid or anhydride with the appropriate alkyl amine under reaction temperatures typically at or near the boiling point of the alkyl amine, preferably from about 30° to about 200° C., followed by removal of excess amine. Certain reactions, do to their exothermic nature, may not require external heating.

The two step procedure involves esterification of the di- or tri-basic organic acid or anhydride with methanol using a boron trifluoride or other Lewis Acid catalyst at a temperature of from about 30° to about 100° C. followed by removal of the excess methanol and catalyst. The resulting trimethyl ester is then amidated as described in the one step process above using the appropriate alkylamine followed by removal of excess amine. Preferably, the alkyl amides of the present invention are nonpolymeric.

When the alkylamide of the present invention is included at lower levels in the composition, a gel is formed. At higher levels, or when other gelling agents are included in the composition, the hardness of the composition is increased, so as to form a hard stick. The alkyl amides of di- and tri-basic carboxylic acids are preferably present at a concentration of from about 0.1% to about 25%, preferably of from about 1% to about 15%, more preferably from about 1% to about 10%.

Anhydrous Liquid carrier

The anhydrous antiperspirant gel compositions of the present invention comprise an anhydrous liquid carrier for the crystalline gellant described hereinbefore, wherein the anhydrous liquid carrier comprises one or more anhydrous liquids which each or collectively have a solubility parameter of from about 3 to about 13 $(cal/cm^3)^{1/2}$, preferably from about 5 to about 11 $(cal/cm^3)^{1/2}$, more preferably from about 5 to about 9 $(cal/cm^3)^{1/2}$. The anhydrous liquid carrier is a liquid under ambient conditions.

Solubility parameters for the liquid carriers or other materials, and means for determining such parameters, are well known in the chemical arts. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

Concentrations of the anhydrous liquid carrier in the antiperspirant gel composition will vary with the type of liquid carrier selected, and the type of gellant used in combination with the liquid carrier, and the solubility of the selected gellant in the selected carrier, and so forth. Preferred concentrations of the anhydrous liquid carrier ranges from about 10% to about 80%, preferably from about 30% to about 70%, more preferably from about 45% to about 70%, by weight of the composition.

The anhydrous liquid carrier preferably comprises one or more anhydrous liquid carriers suitable for topical application to human skin, which carrier or combination of liquid carriers are liquid under ambient conditions. The term "anhydrous" as used herein means that the antiperspirant gel composition of the present invention, and the essential or optional components thereof are substantially free of added or free water. From a formulation standpoint, this means that the antiperspirant gel compositions of the present invention preferably contain less than about 5%, preferably less than about 3%, more preferably less than about 1%, most preferably zero percent, by weight of free or added water. These liquid anhydrous, solvents may be organic or silicone-containing, volatile or non-volatile, polar or nonpolar, provided that the solvent can form a solution or other homogenous liquid or homogenous liquid dispersion with the selected gellant at the selected gellant concentration at a temperature of from about 28° to about 250° C., preferably from about 28° to about 100° C., more preferably from about 28° to about 78° C. The anhydrous liquid solvent preferably has a low viscosity to provide for improved spreading performance on the skin.

The anhydrous liquid carrier preferably comprises a modified or organofunctional silicone carrier selected from the group consisting of polyalkylsiloxanes, polyalkyarylsiloxanes, polyestersiloxanes, polyethersiloxane copolymers, polyfluorosiloxanes, polyaminosiloxanes, and combinations thereof. These modified silicone carriers must be liquid under ambient conditions, and have a viscosity of less than about 100,000 centistokes, preferably less than about 500 centistokes, more preferably from about 1 centistoke to about 50 centistokes, and even more preferably from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

The modified silicone carriers suitable for use in the pharmaceutical compositions include, but are not limited to, compounds or materials as defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/ polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, vinyl, alkoxy, arylalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu ,e.g. Japanese Patent Publication JP86143760 or from Walker Chem. 6MBH (described in EP722970); alkoxysiloxanes; alkoxysilanes; methicones (polymethylalkylsiloxanes); and combinations thereof.

Nonlimiting examples of suitable modified silicone carriers for use in the pharmaceutical compositions herein include the following modified silicones available from Dow Corning: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-190 Fluid (Dimethicone Copolyol); DC-193 Fluid (Dimethicone Copolyol); DC-1401 (Cyclomethicone [and] Dimethiconol); DC-5200 Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-580 Wax (Stearoxytrimethylsilane [and] Stearyl Alcohol); DC-1-3563 (Dimethiconal); DC-X2-1286 (Dimethiconol); DC-X2-1146A (Cylcomethicone [and] Dimethiconol); DC-8820 Fluid (Amino functionalized); DC Q5-0158A wax (stearoxytrimethylsilane); DC-Q2-8220 (Trimethylsilylamodimethicone); DC-7224 (Trimethylsilylamodimethicone); DC-X2-1318 Fluid (Cyclomethicone [and] Vinyldimethicone); DC-QF1-3593A fluid (Trimethylsiloxysilicate) and combinations thereof.

Other nonlimiting examples of suitable modified silicone carriers for use in the pharmaceutical compositions herein include the following modified silicones available from General Electric: GE SF-1023 (Dimethyl-Diphenyl-Siloxane); GE CF-1142 (Methylphenyl Siloxane Fluid); GE SF-1153 (Dimethyl-Diphenyl-Siloxane); GE SF-1265 (Diphenyl-Dimethyl-Siloxane); GE SF- 1328; GE SF-1 188 (Dimethicone copolyol); GE SF-1188A (Silicone polyether copolymer); GE SF- 1288 (silicone polyether copolymer, dimethyl-methyl 3-hydroxypropyl ethoxylated); GE SF-1318 (Methylester Siloxane); GE SF-1328 (silicone surfactant, dimethyl-methyl 3-hydroxypropyl ethoxylated-propoxylated); GE SF-1550 (methylphenyl siloxane, hexamethyl-3-phenyl-3-[[trimethylsilyl]oxy]trisiloxane); GE SF-1632 (silicone wax); GE SS-4267 (Dimethicone [and] Trimethylsiloxysilicate).

Other nonlimiting examples of suitable modified silicone carriers for use in the pharmaceutical compositions herein include the following modified silicones available from Goldschmidt: Abil EM-90 (silicone emulsifier); Abil EM-97 (polyether siloxane); Abil Wax 9810 (silicone wax or C24-28 methicone); Abil Wax 2434 (Stearoxy Dimethicone); Abil Wax 9800D (Stearyl Dimethicone); and Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone Copolymers).

Other nonlimiting examples of suitable modified silicone carriers for use in the pharmaceutical compositions herein include the following: Masil 756 from PPG Industries (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Silicone L-711, L-720, L-721 and L722 (dimethicone copolyols from Union Carbide); Silicone L-7000, L-7001, L-7002, L-7004, L-7500, L-7600, L-7602, L-7604, L-7605, and L-7610 (dimethicone copolyols from Union Carbide); Unisil SF-R (dimethiconol from UPI); Silicate Cluster from Olin (Tris[tributoxysiloxy] methylsilane); silicone copolymer F-754 (dimethicone copoly from SWS Silicones); and combinations thereof.

The anhydrous liquid carrier preferably comprises one or more volatile carriers, optionally in combination with one or more non-volatile carrier. In this context, the term "volatile" refers to carriers having a measurable vapor pressure under ambient conditions, and the term "non-volatile" refers to carriers which do not have a measurable vapor pressure under ambient conditions. These volatile silicone carriers may be cyclic, linear or branched chain silicones having the requisite volatility defined herein. Non-limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicon atoms. Most preferably are those which conform to the formula:

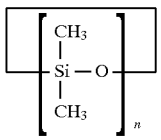

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Coring 344, and Dow Corning 345 (commercially available from Dow Coring Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V ( available from Mazer) and combinations thereof.

The anhydrous liquid carrier may also comprise a non-volatile silicone carrier other than or in addition to the preferred modified silicone carriers described hereinbefore. These non-volatile silicone carriers are preferably linear silicones which include, but are not limited to, those which conform to either of the formulas:

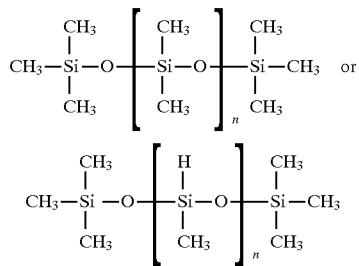

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the antiperspirant compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

The anhydrous liquid carrier may also comprise fluorochemicals such as fluorosurfactants, fluorotelemers, and perfluoropolyethers, some examples of which are described in Cosmetics & Toiletries, Using Fluorinated Compounds in Topical Preparations, Vol. 111, pages 47–62, (Oct. 1996) which description is incorporated herein by reference. More specific examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress ® PFPE oils, and the series fluorosurfactants from Dupont Performance Chemicals under the trade name Zonyl ® Fluorosurfactants.

Suitable organic liquid solvents for use in the composition include saturated or unsaturated, substituted or unsubstituted, branched or linear or cyclic, organic compounds that are also liquid under ambient conditions. These solvents include hydrocarbon oils, alcohols, organic esters and ethers that are liquid under ambient conditions. Preferred organic solvents include mineral oil and other hydrocarbon oils, some examples of which are described in U.S. Pat. No. 5,019,375, issued to Tanner et al. on May 28, 1991, which description is incorporated herein by reference. Other suitable organic liquid solvents include Permethyl 99A, Permethyl 101A (Permethyl available from Persperse Corp.), Isopar series of materials (available from Exxon), isohexadecane, diisopropyl adipate, butyl stearate, isododecane, light mineral oil, petrolatum and other similar materials.

The anhydrous liquids carrier is preferably, substantially free of polar, water immiscible, organic solvents. It has been found that the antiperspirant and deodorant efficacy of the antiperspirant gel or gel-solid stick compositions are improved by minimizing or eliminating the amount of anhydrous polar organic solvent in the composition. In this context, "substantially free" means that the antiperspirant gel or gel-solid stick compositions preferably contain less than 7%, more preferably less than about 3%, even more preferably zero percent, by weight of an anhydrous organic polar solvent. These solvents are liquid under ambient conditions and include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Examples of some anhydrous liquid, polar organic solvents are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

The antiperspirant gel or gel-solid stick compositions of the present invention can be formulated as either a gel or a gel stick, soft gel, cream, lotion or roll-on composition. It is difficult to quantitatively distinguish between an antiperspirant "gel" and an antiperspirant "stick". For example, note the discussion in the article by Schmolka, "Gel Cosmetics", in Cosmetics &. Toiletries, Vol. 99 (November 1984), pp. 69–76. Generally, a gel is more viscous than a liquid, or than a paste which fails to retain its shape. It is not as rigid as a stick. Typically, it is understood that gels are soft, deformable products while sticks are free-standing solids.

Optional Components

Other ingredients conventionally incorporated into the antiperspirant gels and/or gel sticks may also be included. As for the various other ingredients which can be incorporated, attention is directed to such optional components as hardeners, strengtheners, chelating agents, colorants, perfumes, emulsifiers and fillers. These other optional components are further described in U.S. Pat. No. 3,255,082 to Barton; U.S. Pat. No. 4,049,792 to Elsnau; U.S. Pat. No. 4,137,306 to Rubino, et al; U.S. Pat. No. 4,279,658 to Hooper, et al; Canadian Patent 1,164,347 which issued to Beckmeyer et al.; European Patent Application 117,070 which published on Aug. 29, 1984; and Geria, "Formulation of Stick Antiperspirants and Deodorants", Pharmaceuticals and Toiletries, 99: 55–60 (1984), all of which are herein incorporated by reference in their entirety.

Emulsifiers are particularly useful in the present invention. These emulsifiers include non-ionic surfactants useful for forming water-in-oil emulsions. The level of emulsifiers used in the present invention is typically less than about 10%, preferably less than about 5%. Examples of these emulsifiers include polyoxyethylene ethers of fatty alcohols, and polyoxyethylene-polysiloxane copolymers. Such emulsifiers are disclosed by EPO Application 373,424 Raleigh et al., and U.S. Ser. No. 530,671, Cedeno et al., filed Jul. 2, 1991, all of which are herein incorporated by reference in their entirety.

Preferably, when the compositions of the present invention are in the form of a solid emulsion, the compositions include a surfactant. This ensures that the discontinuous phase stays dispersed upon cooling of the composition to form the gel. Preferred for use herein are surfactants which are easily rinsed from the skin.

Thickeners are also useful in the present invention. Their selection and the level at which they are used should be so as not to significantly affect the aesthetics of the gel compositions. Typical levels of thickeners are at levels of less than about 5%. Examples of said thickeners are disclosed in U.S. Pat. No. 4,985,238, Tanner et al., issued Jan. 15, 1991; herein incorporated by reference in its entirety. These thickeners include wax-like materials such as beeswax, cerasin, hydrogenated castor oil, synthetic waxes such as Fisher Tropsch waxes, microcrystalline waxes, polyethylene waxes, and mixtures thereof.

In addition to the alkylamide gelling agent described above, the compositions of the present invention may also incorporate other gelling agents. Suitable additional gelling agents are disclosed in U.S. Pat. No. 5,429,816 to Hofrichter et al., issued July 4, 1995, herein incorporated by reference in its entirety. Gelling agents included therein include those having the formula:

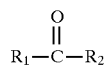

wherein $R_1$ is $OR_2$ or $NR_2R_3$ wherein $R_2$ and $R_3$ are, independently or together, a hydrogen, an aryl, a siloxane, a saturated or unsaturated, substituted or unsubstituted, straight, branched, or cyclic $C_1$–$C_{22}$ alkyl, $C_1$–$C_{22}$ alkoxy, $C_1$–$C_{22}$ alkyl substituted aryl, or $C_1$–$C_{22}$ alkyl substituted aryl radical and wherein $R_2$ is a saturated or unsaturated, substituted or unsubstituted, straight or branched chain $C_1$–$C_{36}$ alkoxy. Preferred gelling agents from among this group include 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, 12-hydroxylauric acid, 16-hydroxyhexadecanoic acid, derivatives thereof and mixtures thereof Also in U.S. Pat. No. 5,429,816 are gelling agents having the formula:

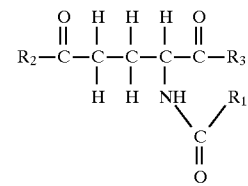

wherein $R_1$ is an alkyl, aryl, arylalkyl radical is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moiety is branched, linear or cyclic and has from about 2 to about 20 carbon atoms. Preferred gelling agents from among this group include N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof. Mixtures of the above described additional gelling agents may also be incorporated into the present invention.

Mixtures of these gelling agents may also be incorporated into the present invention.

Particulate and filler materials may also be included in the present compositions. These materials are typically used at levels of from about 0.5% to about 5%, preferably not more than about 3%. Such materials are disclosed in U.S. Pat. No. 5,019,375, Tanner et al., issued May 28, 1991, herein incorporated by reference in its entirety. Suitable filler materials include collodial silica (such as Cab-O-Sil, sold by Cabot Corp.), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in pharmaceutical sticks is disclosed in U.S. Pat. No. 4,126,679, Davy et al., issued Nov. 21, 1987, incorporated by reference in its entirety. Examples of other particulate materials include particulate hydrophilic polymers such as cellulose ether polymers, modified starches, polyamides, and polypeptides.

A wash-off agent may be utilized to improve the ease with which the ingredients—particularly the gelling agent and the non-polar, non-volatile oils—may be washed off. The wash-off agent is highly preferably a non-liquid. The wash-off agent is typically in the pharmaceutical compositions in an amount from about 0.1% to about 10%.

Typical wash-off agents are non-liquids selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$-preferably, the polyoxyethylene ethers-wherein: $R_1$ and $R_2$ are the same or different alkyl, alkenyl, or aromatic hydrocarbon radical which may be substituted or unsubstituted—preferably an alkyl radical—having from about 4 to about 22 carbon atoms; and n is from about 2 to about 80.

Preferred examples of such wash-off agents include: ceteth-2 through ceteth-30, steareth-2 through steareth-30, ceteareth-2 through ceteareth-30, PEG-2 stearate through PEG-30 stearate, PEG-12 isostearate, PEG-16 hydrogenated castor oil, PEG-40 hydrogenated castor oil, and PEG-20 glyceryl stearate; more preferably, ceteareth-20, steareth-21, PEG-20 stearate, and PEG-16 hydrogenated castor oil; and most preferably, ceteareth-20.

Method of Manufacture

The antiperspirant gel compositions of the present invention may be prepared by any known or otherwise effective technique, suitable for providing an antiperspirant gel composition having the requisite crystalline matrix and other product characteristics described herein. Such methods involve formulation of the essential components of the composition to form a gel having the requisite elastic to viscous moduli ratio, product hardness, and visible residue index, wherein the crystalline matrix within the composition comprises elongated gellant crystals having an aspect ratio of greater than about 2, preferably greater than about 6, and an average particle diameter that is minimized (preferably to less than about 1 $\mu$m) through methods well known in the formulation art for minimizing crystalline particle size in a composition.

Crystalline particle size in the preferred embodiments of the present invention can be determined by techniques well known in the art, which includes light or electron microscopy of the composition, wherein the composition is formulated for analysis purposes without particulate antiperspirant active or other solid particulates. Without such reformulation, it is more difficult to distinguish crystalline gellant particle size and morphology from the particle size and morphology contributed from other non-gellant particulates. The reformulated composition is then evaluated by light or electron microscopy or other similar method.

Methods for preparing the antiperspirant gel compositions of the present invention include those methods well known in the art for formulating compositions containing small gellant crystalline particles. Such methods include the use of nucleating agents, formulation with select carriers or gellants or carrier/gellant combinations, controlling rates of crystallization including controlling formulation, controlling process flow rate, and processing temperatures, and other methods described herein. All such methods should be applied to the formulation to control or minimize gellant crystal particle size, and to form the desired elongated crystalline particles, to form the desired crystalline matrix of the composition.

Method of Use

The antiperspirant gel compositions may be applied topically to the axilla or other area of the skin in an amount effective to treat or reduce perspiration wetness and odor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied to the axilla or other area of the skin, one or two times daily, preferably once daily, to achieve effective antiperspirant and odor control over an extended period.

EXAMPLES

The following non-limiting examples illustrate specific embodiments of the antiperspirant gel compositions of the present invention, including methods of manufacture and use.

Each of the exemplified compositions are prepared by combining all of the listed components except the antiperspirant active and other materials such as perfumes. The combined components are heated to about 100° C. with agitation to form a hot liquid, after which all other materials are added to the heated liquid. The heated liquid is allowed to cool with agitation until just before the point of solidification, at which point the cooled, liquid composition is filled into applicator packages and allowed to cool and solidify to the requisite product hardness.

Table 1 includes examples of gel-solid antiperspirant sticks incorporating the alkylamide gelling agents of the present invention. The compositions are formed by combining and mixing the ingredients of each column using conventional technology.

TABLE 1

| Component | Example I | Example II | Example III | Example IV |
|---|---|---|---|---|
| Cyclomethicone[1] | 45.9 | 48.0 | 47.8 | 42.3 |
| Octyldodecanol[2] | 13.4 | 14.0 | 14.0 | 4.0 |
| Petrolatum[3] | — | — | — | 16.5 |
| 12-Hydroxystearic Acid[4] | 9.8 | — | 6.8 | 6.8 |
| C20–40 alcohols[5] | 0.5 | 0.5 | 0.5 | — |
| 2-Dodecyl-N,N'-dibutylsuccinamide | 3.2 | 9.0 | 2.2 | 1.1 |
| 2-Dodecyl-N,N'-dihexylsuccinamide | — | — | — | 1.1 |
| C20–40 Pareth-10[6] | 1.2 | 1.25 | 1.25 | — |
| C20–40 Pareth-40[7] | 1.2 | 1.25 | 1.25 | — |
| C20–40 Pareth-3[8] | — | — | — | 2.0 |
| Perfume | | | | |
| Al Zr tri chlorohydrex glycinate[9] | 24.8 | 26.0 | 26.0 | 26.0 |
| Disodium EDTA[10] | — | — | 0.2 | 0.2 |
| Stearyl Alcohol[11] | — | — | — | — |

[1]Dow Corning 245 Fluid; General Electric SF-1202
[2]Jarchem Jarcol I-20
[3]Witco White Perfecta
[4]Acme Hardesty
[5]Petrolite Unilin 425
[6]Petrolite Unithox 450
[7]Petrolite Unithox 480
[8]Petrolite Unithox 320
[9]Supplied by Westwood Chemical Corporation
[10]Supplied by Ciba-Geigy
[11]Witco

TABLE 2

| Component | Example V | Example VI | Example VII | Example VIII |
|---|---|---|---|---|
| Cyclomethicone[1] | 57.6 | 58.0 | 55.8 | 52.8 |
| Octyldodecanol[2] | 13.4 | 14.0 | 14.0 | 4.0 |

TABLE 2-continued

| Component | Example V | Example VI | Example VII | Example VIII |
|---|---|---|---|---|
| Petrolatum[3] | — | — | — | 16.5 |
| 12-Hydroxystearic Acid[4] | 1 | — | 0.7 | 3.5 |
| C20–40 alcohols[5] | 0.5 | — | 0.5 | — |
| 2-Dodecyl-N,N'-dibutylsuccinamide | 0.3 | 2.0 | 0.2 | 0.5 |
| 2-Dodecyl-N,N'-dihexylsuccinamide | — | — | — | 0.5 |
| C20–40 Pareth-10[6] | 1.2 | — | 1.25 | — |
| C20–40 Pareth-40[7] | 1.2 | — | 1.25 | — |
| C20–40 Pareth-3[8] | — | — | — | 2.0 |
| Perfume | | | | 0.1 |
| Al Zr tri chlorohydrex glycinate[9] | 24.8 | 26.0 | 26.0 | 20.0 |
| Disodium EDTA[10] | — | — | 0.2 | 0.2 |
| Stearyl Alcohol[11] | — | — | — | — |

[1]Dow Corning 245 Fluid; General Electric SF-1202
[2]Jarchem Jarcol I-20
[3]Witco White Perfecta
[4]Acme Hardesty
[5]Petrolite Unilin 425
[6]Petrolite Unithox 450
[7]Petrolite Unithox 480
[8]Petrolite Unithox 320
[9]Supplied by Westwood Chemical Corporation
[10]Supplied by Ciba-Geigy
[11]Witco

What is claimed is:

1. An antiperspirant composition comprising:
   (A) an antiperspirant active;
   (B) from about 0.1% to about 25% by weight of a gellant of the formula:

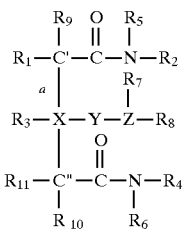

(a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;
   (b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;
   (c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers;
   (d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;
   (e) $R_9$ is nil or hydrogen;
   (f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl;
   (g) X is nil, nitrogen, aryl or 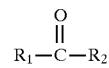 where n is an integer from 1 to 6;
   (h) Y is nil, acyl or carbonyl;
   (i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl; and
   (j) "a" is a double or single bond provided:
      (i) when X is nil, Y, Z, $R_3$, $R_7$ and $R_8$ are nil, C' is bonded directly to C" and $R_1$ is not a hydrogen;
      (ii) when X and Z are not nil and Y is nil, X is directly bonded to Z;
      (iii) when Z is nil, a hydrogen or a hydroxy, $R_7$ and $R_8$ are nil; and
      (iv) when "a" is a double bond, $R_3$ and $R_9$ are nil; and
   (C) an anhydrous liquid carrier.

2. An antiperspirant composition according to claim 1, wherein the gelling agent is selected from the group consisting of alkyl amides of citric acid, tricarballylic acid, aconitic acid, nitrilotriacetic acid, alkylamides of alkyl succinic acid, alkylamides of alkenyl succinic acid and anhydrides thereof.

3. An antiperspirant composition according to claim 2, further comprising from about 1% to about 15% by weight of a secondary gelling agent having the formula:

$$R_1 - \overset{O}{\underset{\|}{C}} - R_2$$

wherein $R_1$ is $OR_2$ or $NR_2R_3$ wherein $R_2$ and $R_3$ are, independently or together, a hydrogen, an aryl, a siloxane, a saturated or unsaturated, substituted or unsubstituted, straight, branched, or cyclic $C_1$–$C_{22}$ alkyl, $C_1$–$C_{22}$ alkoxy, $C_1$–$C_{22}$ alkyl substituted aryl, or $C_1$–$C_{22}$ alkyl substituted aryl radical and wherein $R_2$ is a saturated or unsaturated, substituted or unsubstituted, straight or branched chain $C_1$–$C_{36}$ alkoxy.

4. An antiperspirant composition according to claim 3, wherein the secondary gelling agent is selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, 12-hydroxylauric acid, 16-hydroxyhexadecanoic acid, derivatives thereof and mixtures thereof.

5. An antiperspirant composition according to claim 1, further comprising an additional gelling agent having the formula:

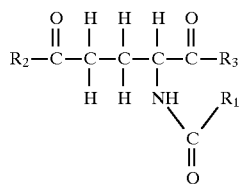

wherein $R_1$ is an alky, aryl, arylalkyl radical is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moiety is branched, linear or cyclic and has from about 2 to about 20 carbon atoms.

6. An antiperspirant composition according to claim 5, wherein the additional gelling agent is selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-.

7. An antiperspirant composition according to claim 6 wherein the anhydrous carrier has a solubility parameter of from about 3 to about 13 $(cal/cm^3)^{1/2}$.

8. An antiperspirant composition according to claim 7 wherein the anhydrous carrier is selected from the group consisting of: nonpolar, volatile oils; relatively polar, non-volatile oils; nonpolar, non-volatile oils; and mixtures thereof.

9. An antiperspirant composition according to claim 8 wherein the nonpolar, volatile oils are selected from the group consisting of non-volatile polysiloxanes, paraffinic hydrocarbon oils, and mixtures thereof.

10. An antiperspirant composition according to claim 9 wherein the non-volatile polysiloxanes are selected from the group consisting of polyalkylsiloxanes, polyarylsiloxanes, polyalkylarylsiloxanes, polyethersiloxane copolymers, polyfluorosiloxanes, polyaminosiloxanes and mixtures thereof.

11. An antiperspirant composition according to claim 10, wherein the paraffinic hydrocarbon oil is selected from the group consisting of mineral oils, petrolatums, isodecanes, permethyls, isohexadecanes, isododecane, isoparaffins.

12. An antiperspirant composition according to claim 1, wherein the carrier is in the form of a gel, soft gel, cream, lotion, roll-on ,or gel-solid stick.

13. An antiperspirant composition according to claim 12, wherein the carrier forms a gel stick.

14. An antiperspirant composition according to claim 13 wherein the antiperspirant active is selected from the group consisting of aluminum halides, aluminum hydroxyhalides, aluminum chlorohydrate, zirconyl oxyhalides, zirconyl hydroxyhalides, and mixtures thereof.

15. An antiperspirant composition according to claim 14 wherein the antiperspirant active is particulate.

16. An antiperspirant composition comprising:
 (a) an antiperspirant active:
 (b) from about 0.1% to about 25% by weight of a non-triglyceride gelling agent compound, comprising:
  (i) a $C_2$–$C_{12}$ linear backbone having terminal hydrogen bonding functional groups, each hydrogen bonding functional group carrying thereon a non-polymeric, organic side chain; and
  (ii) an additional non-polymeric, organic side chain attached to the backbone by an acyl-amide functional group such that the acyl portion of the acyl-amide functional group attaches to the backbone
 wherein the side chains of the hydrogen bonding functional groups are disposed on the same axial side of the backbone such the additional side chain is disposed on a planar side opposite the side chains of the hydrogen bonding functional groups; and
 (c) an anhydrous liquid carrier.

17. An antiperspirant composition according to claim 16, wherein the side chains of the hydrogen bonding functional group are attached to the hydrogen bonding functional group by acyl-amide functional groups such that the acyl portion of the acyl-amide functional group attaches to the hydrogen bonding functional group.

* * * * *